(12) United States Patent
Furuichi et al.

(10) Patent No.: US 9,295,450 B2
(45) Date of Patent: Mar. 29, 2016

(54) IMAGING APPARATUS AND CONTROL METHOD THEREOF

(75) Inventors: Junya Furuichi, Kanagawa (JP); Yuuji Onimura, Kanagawa (JP)

(73) Assignee: TERUMO KABUSHIKI KAISHA, Shibuya-Ku, Tokyo (JP)

( * ) Notice: Subject to any disclaimer, the term of this patent is extended or adjusted under 35 U.S.C. 154(b) by 1234 days.

(21) Appl. No.: 13/230,266

(22) Filed: Sep. 12, 2011

(65) Prior Publication Data

US 2012/0063570 A1  Mar. 15, 2012

Related U.S. Application Data

(63) Continuation of application No. PCT/JP2010/000526, filed on Jan. 29, 2010.

(30) Foreign Application Priority Data

Mar. 12, 2009  (JP) .................................. 2009-060095

(51) Int. Cl.
*A61B 6/00* (2006.01)
*A61B 6/12* (2006.01)
*A61B 8/06* (2006.01)
(Continued)

(52) U.S. Cl.
CPC ................. *A61B 8/4461* (2013.01); *A61B 6/12* (2013.01); *A61B 6/487* (2013.01); *A61B 6/504* (2013.01); *A61B 6/5247* (2013.01); *A61B 6/54* (2013.01); *A61B 8/06* (2013.01); *A61B 8/0891* (2013.01); *A61B 8/12* (2013.01); *A61B 8/5238* (2013.01); *A61B 8/54* (2013.01)

(58) Field of Classification Search
CPC .......... A61B 6/12; A61B 6/487; A61B 6/504; A61B 6/5247; A61B 6/54; A61B 8/06; A61B 8/0891; A61B 8/12; A61B 8/4461; A61B 8/5238; A61B 8/54

See application file for complete search history.

(56) References Cited

U.S. PATENT DOCUMENTS 5,357,550 A * 10/1994 Asahina ................. A61B 6/481
378/98.2
6,152,877 A  11/2000 Masters
(Continued)

FOREIGN PATENT DOCUMENTS

JP  10-137238 A  5/1998
JP  3167367 B2  3/2001
(Continued)

OTHER PUBLICATIONS

International Search Report (PCT/ISA/210) issued on Feb. 23, 2010, by Japanese Patent Office as the International Searching Authority for International Application No. PCT/JP2010/000526.

*Primary Examiner* — Glen Kao
(74) *Attorney, Agent, or Firm* — Buchanan Ingersoll & Rooney PC

(57) ABSTRACT

The present invention discloses an imaging apparatus radial-operating a transmitting and receiving unit and generating cross-sectional images inside the body cavity by a plurality of images, which includes: an X-ray image memory holding a plurality of X-ray images obtained by X-ray imaging the transmitting and receiving unit inside the body cavity by a predetermined imaging cycle, an image processing unit generating a cross-sectional moving image by setting the rotation cycle of the transmitting and receiving unit to be frame rate, and an image processing unit reading out an X-ray image, obtained from X-ray imaging just previously at every timing for every rotation cycle of the transmitting and receiving unit, from the X-ray image memory and generating an X-ray moving image by the frame rate.

14 Claims, 12 Drawing Sheets

(51) Int. Cl.
*A61B 8/12* (2006.01)
*A61B 8/00* (2006.01)
*A61B 8/08* (2006.01)

(56) References Cited

U.S. PATENT DOCUMENTS

2008/0306766 A1  12/2008  Ozeki et al.
2012/0029339 A1* 2/2012  Cohen ................... A61B 6/12
                                               600/407
2013/0216025 A1* 8/2013  Chan ..................... A61B 6/488
                                               378/63
2015/0087980 A1* 3/2015  Yao ...................... A61B 8/463
                                               600/440

FOREIGN PATENT DOCUMENTS

JP    2002-532174 A    10/2002
JP    2005-103018 A     4/2005
JP    2008-301984 A    12/2008

* cited by examiner

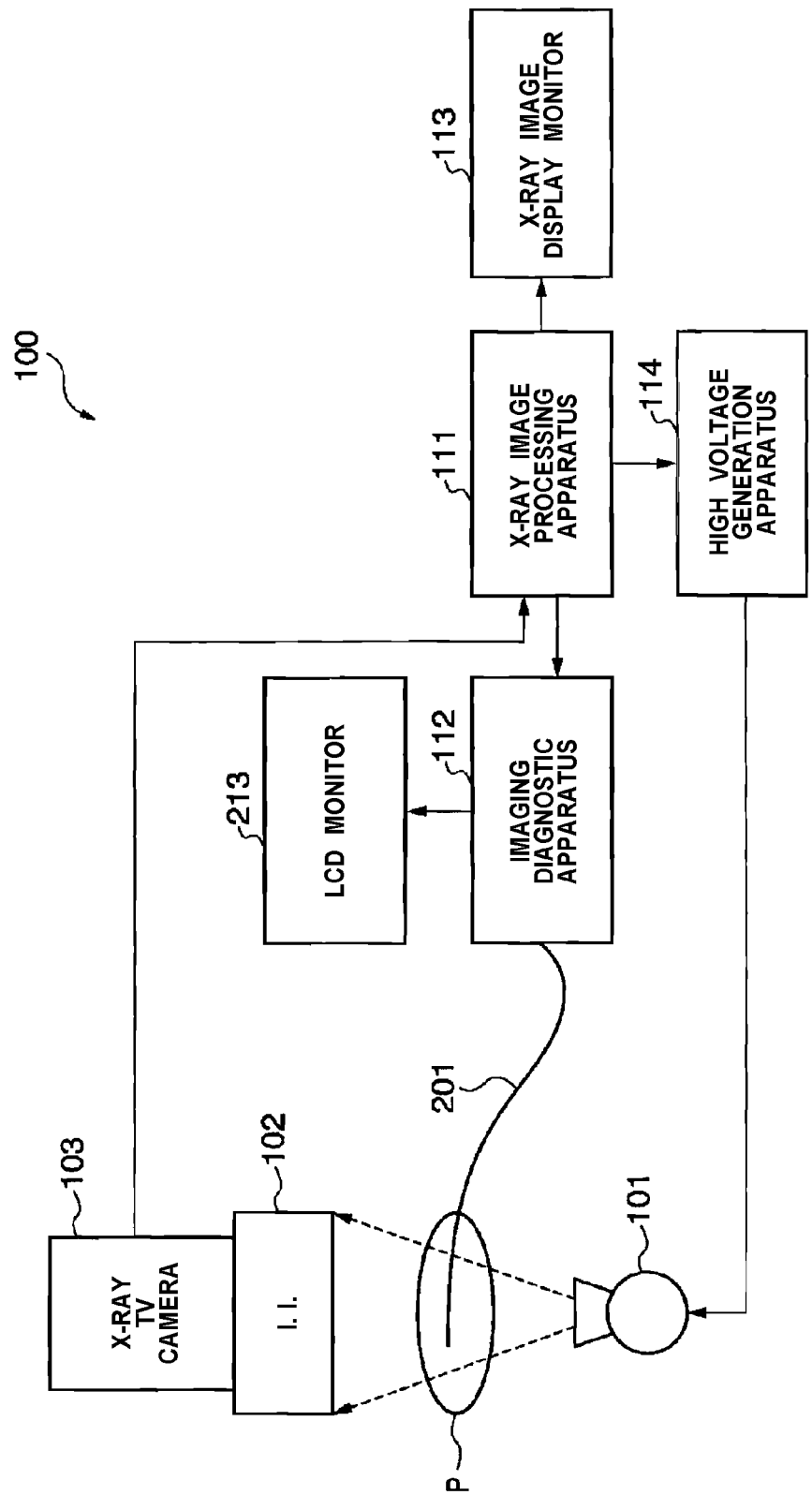

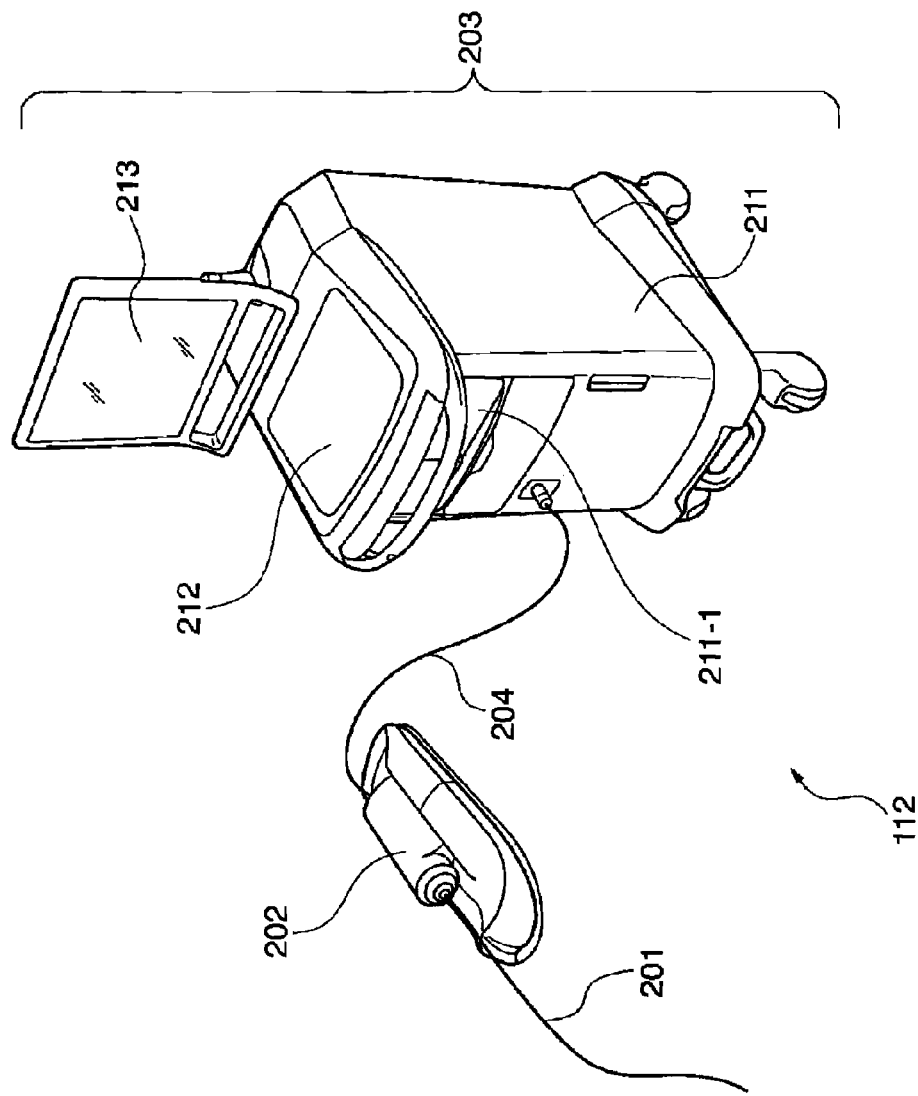

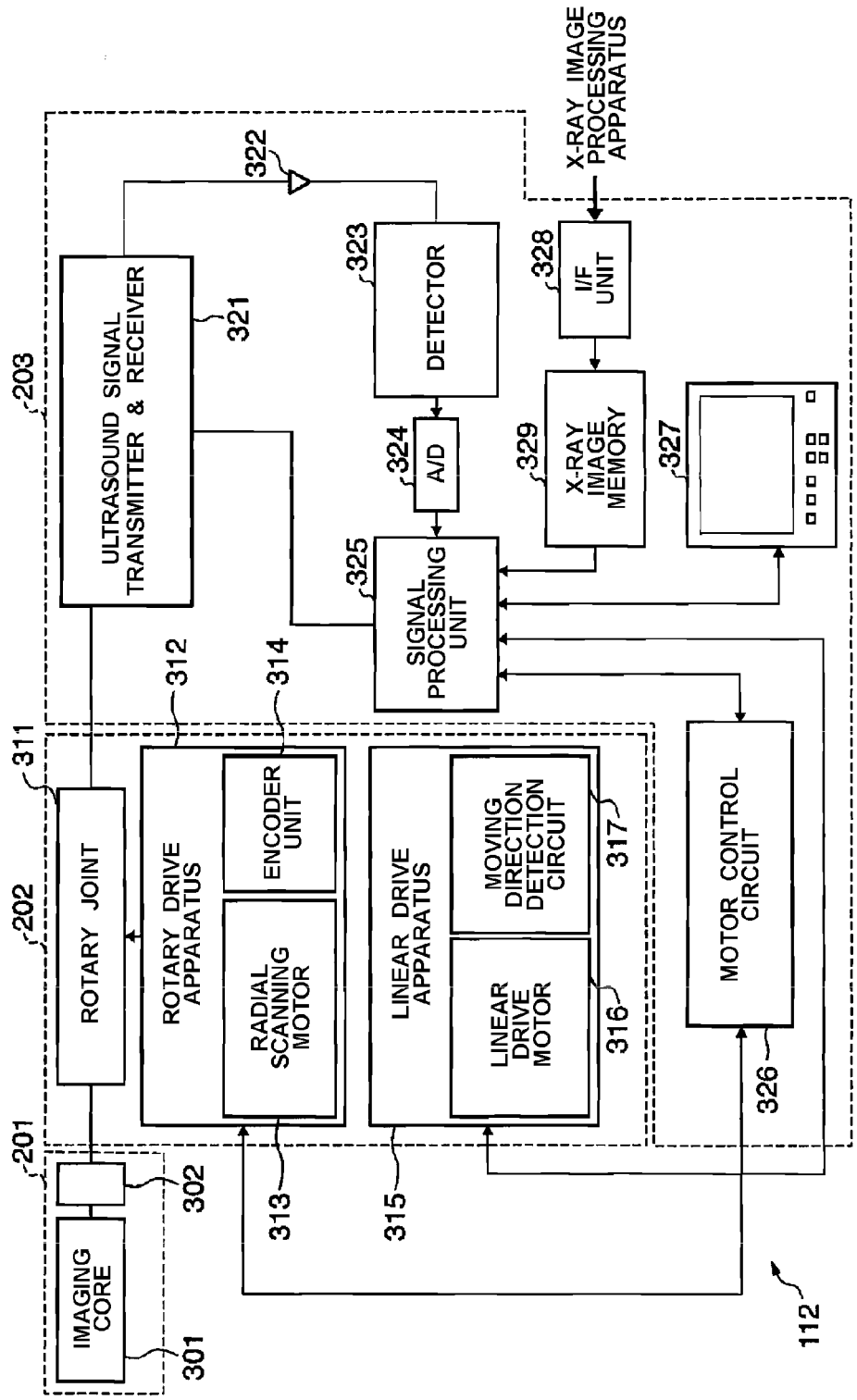

X-RAY IMAGE   CROSS-SECTIONAL
              IMAGE

IMAGING APPARATUS AND CONTROL METHOD THEREOF

This application is a continuation of International Application No. PCT/JP2010/000526 filed on Jan. 29, 2010, and claims priority to Japanese Application No. 2009-060095 filed on Mar. 12, 2009, the entire content of both of which is incorporated herein by reference.

TECHNOLOGICAL FIELD

The present invention relates to an imaging apparatus and a control method for controlling an imaging apparatus.

BACKGROUND DISCUSSION

Imaging apparatus have been widely used for diagnosis of arteriosclerosis, for diagnosis before operation at the time of an endovascular treatment by a high functional catheter such as a balloon catheter, a stent and the like, or for confirming the result after an operation.

An example of an imaging apparatus for diagnosis is an intravascular ultrasound (IVUS) apparatus. Generally, the intravascular ultrasound apparatus radial-operates an ultrasonic probe unit installed with a transmitting and receiving unit composed of an ultrasound transducer inside a blood vessel, a reflected wave (ultrasonic echo) reflected by a biological tissue inside a body cavity of a test subject is received by the transmitting and receiving unit and thereafter, based on the intensity of an ultrasonic echo signal generated by applying a process of amplification, detection or the like, a cross-sectional image of the blood vessel is to be visualized.

Also, another known imaging apparatus is an optical coherent tomography (OCT) apparatus which carries out diagnostic imaging by utilizing coherence of light.

The optical coherent tomography apparatus is an apparatus in which a measurement light is emitted inside a blood vessel while rotating a transmitting and receiving unit while inserting an optical probe unit which is built-in with the transmitting and receiving unit mounted with an optical lens and an optical mirror at the distal end and an optical fiber inside the blood vessel, a radial scan is carried out with receiving reflected light from a biological tissue, and a cross-sectional image of the blood vessel is visualized based on interference signal obtained by making the reflected light obtained depending on this radial scan and a reference light split from the measurement light beforehand interfere each other.

Further, recently, as an enhancement of the optical coherent tomography apparatus, there has been developed an optical frequency domain imaging (OFDI) apparatus which utilizes wavelength sweep.

With respect to the optical frequency domain imaging apparatus utilizing wavelength sweep, the basic constitution is similar as that of the optical coherent tomography apparatus, but a light source having a longer wavelength compared with the optical coherent tomography apparatus is used and also, light having different wavelengths is emitted continuously. Then, mechanism for variably changing the optical path length of the reference light is made unnecessary by employing a constitution in which reflected-light intensity at each point in the depth direction of the biological tissue is found out by frequency analysis of interference signal.

In the description hereinafter, the intravascular ultrasound (IVUS) apparatus, the optical coherent tomography (OCT) apparatus and the optical frequency domain imaging (OFDI) apparatus utilizing wavelength sweep are named generically and referred to as an "imaging apparatus".

Generally, when visualizing a cross-sectional image by using those imaging apparatuses, an X-ray image processing apparatus is used together concurrently. This is because it is effective for making a decision about the treatment region or the like while seeing an angiographic image generated in the X-ray image processing apparatus, and for confirming the contrast marker which the ultrasonic probe unit or the optical probe unit possesses based on the angiographic image and comprehending the position of the ultrasonic probe unit or the optical probe unit. Consequently, it is desirable for the angiographic image (X-ray image) generated in the X-ray image processing apparatus and the cross-sectional image visualized by using the imaging apparatus to be stored and displayed by being mutually correlated with each other.

With this back ground, for example, Japanese Patent No. 3167367 proposes a method in which an angiographic image generated in an X-ray image processing apparatus and a cross-sectional image visualized in an intravascular ultrasound apparatus are held and displayed by being mutually correlated with each other.

SUMMARY

However, in case of the Patent Document described above, there is a premise that the imaging cycle of the angiographic image generated in the X-ray image processing apparatus and the visualizing cycle of the cross-sectional image visualized for every one rotation of the probe in the imaging apparatus (that is, rotation cycle) coincide with each other.

Consequently, in a case, for example, in which the imaging cycle and the rotation cycle are different, when the display of the angiographic image and the cross-sectional image is renewed or a storage process thereof is executed in conformity with the rotation cycle, there can occur such a situation that there is no angiographic image corresponding to the timing when the cross-sectional image is visualized. Also, when employing a constitution in which the display of the angiographic image and the cross-sectional image is renewed or the storage process thereof is performed in conformity with the imaging cycle, there can occur such a situation that there is no angiographic image corresponding to the timing when the cross-sectional image is visualized.

In this case, it results in that usability of a user is lost considerably such that it becomes difficult to specify a position to which the visualized cross-sectional image corresponds inside the blood vessel, such that it becomes difficult to search a corresponding cross-sectional image in a case in which a cross-sectional image at a desired position is required to be watched, or the like.

The present invention was invented in view of the problem described above and addressed to improve usability of a user in an imaging apparatus in which an X-ray image generated in an X-ray image processing apparatus and a cross-sectional image generated in an imaging apparatus are stored and displayed by being mutually correlated with each other.

An imaging apparatus relating to the present invention includes the following constitutions. More specifically, in an imaging apparatus in which by moving a transmitting and receiving unit of a probe including the transmitting and receiving unit for carrying out signal transmission and reception continuously in a longitudinal direction inside a body cavity (e.g., blood vessel) while rotating it, a reflection signal is obtained from the body cavity inside, and based on the obtained reflection signal, cross-sectional images inside the body cavity are generated in the longitudinal direction by a plurality of images, there are provided:

a holding unit for holding a plurality of X-ray images obtained by X-ray imaging of the transmitting and receiving unit inside the body cavity in an imaging cycle defined beforehand, a first generation unit for generating a cross-sectional moving image by using the cross-sectional image generated for every of the rotation cycles by setting the rotation cycle of the transmitting and receiving unit as frame rate a second generation unit for reading out an X-ray image obtained by an X-ray imaging just previously from the holding unit at every timing for every rotation cycle of the transmitting and receiving unit and for generating an X-ray moving image by setting the rotation cycle of the transmitting and receiving unit as frame rate by using the read out X-ray image, and a display unit for displaying the cross-sectional moving image and the X-ray moving image by the frame rate.

According to the present invention, it becomes possible to improve usability of a user in an imaging apparatus in which an X-ray image generated in an X-ray image processing apparatus and a cross-sectional image generated in an imaging apparatus are stored and displayed by being mutually correlated with each other.

Other features and advantages of the present invention will become clear according to the following explanations with reference to the attached drawings. It should be noted in the attached drawings that identical reference numbers are attached for the identical or similar constitutions.

BRIEF DESCRIPTION OF THE DRAWINGS

The accompanying drawings are included in the specification, constitute a portion of the specification, illustrate embodiments disclosed by way of example, and are referenced in the description below explaining principles and aspects of the imaging apparatus and method disclosed here.

FIG. 1 is a schematic illustration of the construction of an imaging system including an imaging apparatus according to one embodiment disclosed by way of example.

FIG. 2A is a perspective view of an outward appearance and construction of an imaging apparatus.

FIG. 3 is a schematic illustration of features of an intravascular ultrasound apparatus disclosed here.

DETAILED DESCRIPTION

First Embodiment

1. Construction of Imaging System

Figure 2B:
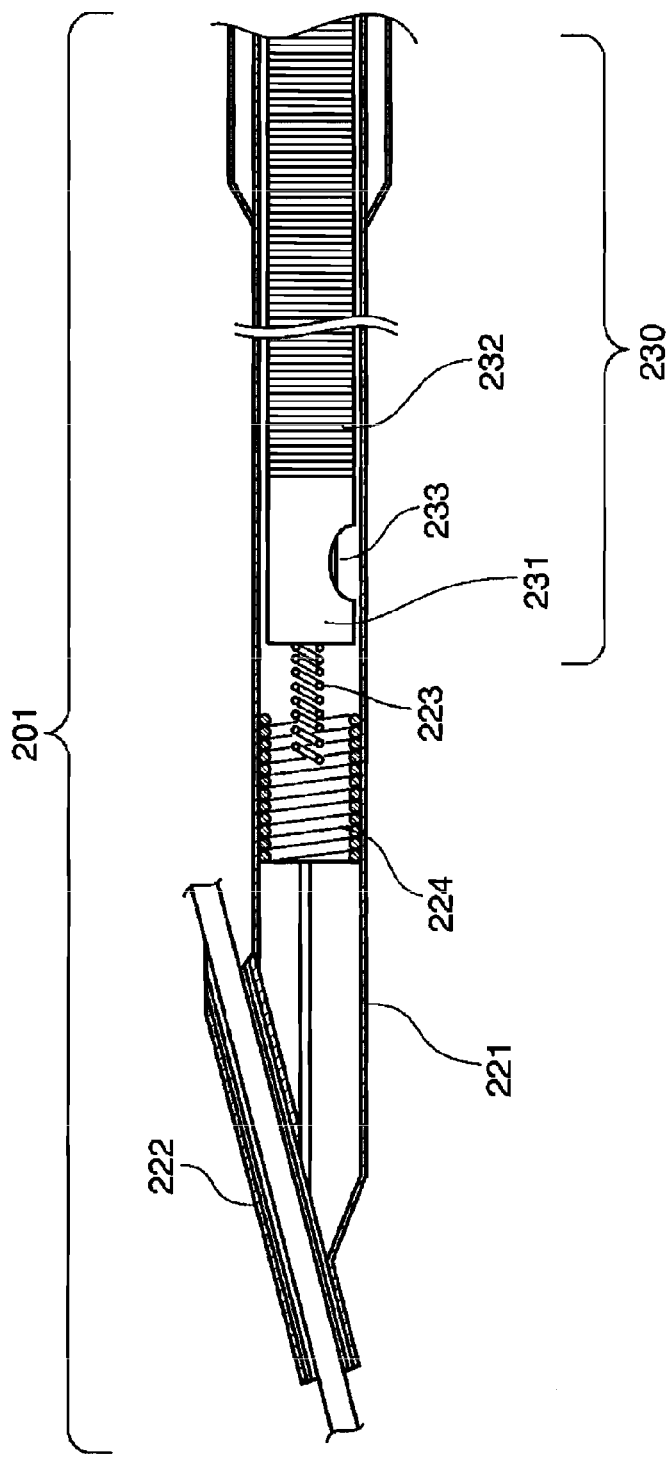
FIG. 2B is a partial longitudinal cross-sectional view of the distal end portion of an optical probe unit.

FIG. 1 illustrates an imaging system 100 including an imaging apparatus 112 according to a first embodiment disclosed by way of example.

In the imaging system 100, X-ray illuminated from an X-ray tube 101 toward a subject body P penetrates the subject body P and thereafter, enters an I.I. (image intensifier) 102. In the I.I. 102, the entered X-ray is converted to an optical image. Also, in the X-ray television camera 103, the optical image converted is further converted to a video signal (signal included with a plurality of X-ray images and information relating to respective imaging timings). Further, the converted video signal is transmitted to an X-ray image processing apparatus 111 where image processings involving, for example, noise correction and tone correction are applied to the video signal.

As shown in FIG. 1, in the imaging system 100, the X-ray image processing apparatus 111 is connected in a communicating manner with an imaging diagnostic apparatus 112. The imaging diagnostic apparatus 112 receives a video signal (signal included with information relating to plurality of X-ray images and respective imaging timings) which is transmitted from the X-ray image processing apparatus 111.

The imaging diagnostic apparatus 112 is configured to store and display the received X-ray image and the visualized cross-sectional image by being mutually correlated with each other. Specifically, the received X-ray image is inputted to an analogue-digital (A-D) converter for X-ray arranged inside the imaging diagnostic apparatus 112, is digitalized and thereafter, is stored in an X-ray image memory by being correlated with the visualized cross-sectional image. Then, the X-ray image stored in the X-ray image memory is displayed on a LCD monitor 213 constituting a portion of the imaging diagnostic apparatus 112 (details thereof will be described later) together with the cross-sectional image.

Further, as shown in FIG. 1, the imaging system 100 includes an X-ray image display monitor 113, apart from the LCD monitor 213 of the imaging diagnostic apparatus 112, for displaying a video signal applied with image processing such as noise correction, tone correction and the like in the X-ray image processing apparatus 111.

Further, the X-ray image processing apparatus 111 is connected with a high voltage generation apparatus 114 which generates high voltage for emitting X-rays at the X-ray tube 101.

In the imaging system 100, a continuous X-ray is usually used on an occasion of the X-ray imaging, but it is also possible to use pulse shaped X-rays in order to obtain an X-ray image in which there is little movement blur. In the case of using the pulse shaped X-ray, the high voltage generation apparatus 114 transmits a pulse signal synchronized with the video signal to the X-ray tube 101 based on instruction from the X-ray image processing apparatus 111.

Additional details and aspects of the imaging diagnostic apparatus 112 in the imaging system 100, including the construction described above, is set forth below. In the case of this exemplified embodiment, the imaging apparatus 112 includes or encompasses an ultrasound imaging apparatus, an optical coherent tomography apparatus, and an optical frequency domain imaging apparatus utilizing wavelength sweep or the like.

2. Outward Appearance Constitution of Imaging Apparatus

FIG. 2A is a diagram showing an outward appearance constitution of an imaging apparatus (ultrasonographic apparatus, optical coherent tomography apparatus or optical frequency domain imaging apparatus utilizing wavelength sweep) 112 relating to a first exemplified embodiment of the present invention.

As shown in FIG. 2A, the imaging apparatus 112 is provided with an ultrasonic probe unit or optical probe unit 201, a scanner and pull-back unit 202 and a steering control apparatus 203. The scanner & pull-back unit 202 and the steering control apparatus 203 are connected by means of a signal wire 204.

The ultrasonic probe unit or optical probe unit 201 is inserted directly into a blood vessel (body cavity) and a state inside the blood vessel is measured or determined by using a transmitting and receiving unit. The scanner and pull-back unit 202 is removable with respect to the ultrasonic probe unit or optical probe unit 201 in which a motor is built-in and radial operation of the transmitting and receiving unit inside the ultrasonic probe unit or optical probe unit 201 is defined.

The steering control apparatus 203 operates to permit inputting of various kinds of setting values on an occasion when visualizing a cross-sectional image inside a blood vessel and also operates to process data obtained by the measurement and displaying the data as a cross-sectional image.

The steering control apparatus 203 includes a main body control unit 211 which, for example, processes data obtained by measurement and outputs the processed result. The steering control apparatus 203 also includes a printer and DVD recorder 211-1 which, for example, prints the process result in the main body control unit 211 and stores it as data.

A user is able to input various kinds of setting values through an operation panel 212, and a LCD monitor 213 serving as a display apparatus displays the process result in the main body control unit 211.

3. Construction of Distal End Portion of Ultrasonic Probe Unit or Optical Probe Unit Set forth below is a description of the construction of the distal end portion of the optical probe unit 201, referring to FIG. 2B. Both an ultrasonic probe unit and an optical probe unit have similar constructions and so the following description of the optical probe unit also applies to the ultrasonic probe unit.

As shown in FIG. 2B, in the inside of a lumen of a catheter sheath 221, there is positioned an imaging core 230 including a housing 231 arranged with a transmitting and receiving unit 233 for transmitting and receiving measurement light and a drive shaft 232 transmitting drive force for rotating it approximately over full length thereof, and an optical probe unit 201 is formed thereby.

The transmitting and receiving unit 233 is installed with an optical mirror for laterally reflecting optical axis of the measurement light transmitted by an optical fiber into which the drive shaft 232 is inserted.

In the transmitting and receiving unit 233, the measurement light is transmitted toward the tissue inside the body cavity and concurrently, reflected light from the tissue inside the body cavity is received.

The drive shaft 232 is coil-shaped and in the inside thereof, there is arranged a signal wire (single mode fiber).

The housing 231 forms a shape including a cut portion at a portion of a short cylindrical shaped metal pipe and is shaped by a cutting-out from a piece of metal, MIM (metal powder injection molding) or the like. The housing 231 includes the transmitting and receiving unit 233 in the inside, and the proximal end side thereof is connected with the drive shaft 232, and a short coil shaped elastic member 223 is provided on the distal end side thereof.

The elastic member 223 is a member obtained by forming a stainless steel wire material in a coil shape. Owing to a fact that the elastic member 223 is arranged on the distal end side, stability on an occasion of the rotation of the imaging core 230 is improved.

A reinforcing coil 224 is provided to help prevent rapid bending of the distal end portion of the catheter sheath 221.

A tube for guide wire lumen 222 includes a lumen for guide wire into which a guide wire is insertable. The tube for guide wire lumen 222 is used for accepting the guide wire inserted beforehand into the body cavity and for guiding the catheter sheath 221 until the target lesion depending on the guide wire.

It is possible for the drive shaft 232 to perform rotational movement and longitudinal movement with respect to the catheter sheath 221, and it is constructed as a multiple and multi-layered closely-attached coil or the like composed of, for example, a metal wire of a stainless metal or the like, which is flexible and also has a characteristic in which rotation is well transmissible.

With respect to the distal end portion of the optical probe unit 201, in order to make it possible to confirm the position of the distal end portion of the imaging core 230 under an X-ray illumination, it is preferable for the elastic member 223 and the housing 231 to be attached with a contrast marker composed of gold, platinum, tungsten or the like. That is, a contrast marker is attached to the elastic member 223 and the housing 231.

4. Features and Aspects of Intravascular Ultrasound Apparatus

Referring to FIG. 3, within the imaging apparatus 112 relating to this embodiment disclosed by way of example, set forth below is a description of features and aspects of a main functional constitution of an intravascular ultrasound (IVUS) apparatus.

FIG. 3 is a diagram schematically illustrating features and aspects of an intravascular ultrasound apparatus 112 shown in FIG. 2A. The intravascular ultrasound apparatus 112 includes an optical probe unit 201, a scanner and pull-back unit 202 and a steering control apparatus 203.

The ultrasonic probe unit 201 is provided with an imaging core 301 including a transmitting and receiving unit composed of an ultrasonic transducer in the inside of the distal end. When the distal end of the ultrasonic probe unit 201 is positioned in a blood vessel (body cavity), the imaging core 301 transmits ultrasonic wave in the cross-sectional direction (emission direction) of the blood vessel based on pulse wave transmitted from an ultrasound signal transmitter and receiver 321, concurrently, receives the reflected wave (ultrasonic echo) thereof, and transmits it to the ultrasound signal transmitter and receiver 321 as an ultrasonic echo signal through a connector unit 302 and a rotary joint 311.

The scanner and pull-back unit 202 includes a rotary joint 311, a rotary drive apparatus 312 and a linear drive apparatus 315. The imaging core 301 inside the ultrasonic probe unit 201 is mounted rotatably by the rotary joint 311 coupling between a non-rotation unit and a rotation unit, and it is driven rotationally by a radial scanning motor 313. By virtue of the imaging core 301 being rotated inside the blood vessel centering around the axis of the ultrasonic probe unit 201, the ultrasound signal is scanned in the circumferential direction and depending on this, it is possible to obtain ultrasonic echo signals necessary for visualization of the cross-sectional image at a predetermined position inside the blood vessel.

The operation of the radial scanning motor 313 is controlled based on a control signal transmitted from a signal processing unit 325 through a motor control circuit 326. Also, the rotation angle of the radial scanning motor is detected by an encoder unit 314. An output pulse which is outputted in the encoder unit 314 is inputted to the signal processing unit 325 and is utilized as a signal reading-out timing for a cross-sectional image display.

The scanner and pull-back unit 202 further includes a linear drive apparatus 315 and defines movement (longitudinal motion) in the longitudinal direction (distal direction inside the body cavity and opposite direction thereof) of the ultrasonic probe unit 201 based on an instruction or input from a signal processing unit 325. The longitudinal motion is produced by the linear drive motor 316 operating based on the control signal from the signal processing unit 325. Also, the longitudinal direction (distal direction inside the body cavity or opposite direction thereof) is detected by a moving direction detector 317 and a detected result thereof is inputted to the signal processing unit 325. A control circuit (driver) of the linear drive motor 316 is installed inside the linear drive apparatus 315, but here a graphical indication of this is not included.

It is possible for the radial scanning motor 313 and the linear drive motor 316 to be connected removably or to be constituted integrally. Also, it is possible for the longitudinal motion by the linear drive motor 316 to be realized by a ball screw or the like. Also, the moving direction detector 317 can be realized, for example, by mounting an encoder on the linear drive motor 316. More specifically, it is possible to detect the longitudinal motion by detecting the rotation direction of the linear drive motor 316.

The ultrasound signal transmitter and receiver 321 includes a transmitting circuit and a receiving circuit. The transmitting circuit transmits a pulse wave to the imaging core 301 inside the ultrasonic probe unit 201 based on a control signal transmitted from a signal processing unit 325.

Also, the receiving circuit receives an ultrasonic echo signal detected by the imaging core 301 inside the optical probe unit 201. The received ultrasonic echo signal is amplified by an amplifier 322.

Further, in the A/D converter 324, the ultrasonic echo signal outputted from the amplifier 322 is applied with sampling and digital data (ultrasonic echo data) of one line is generated.

The ultrasonic echo data of one line unit, which are generated in the A/D converter 413 are inputted into a signal processing unit 325. In the signal processing unit 325, the ultrasonic echo data are detected, and cross-sectional images at respective positions inside the blood vessel are visualized and outputted to a LCD monitor 327 (corresponding to reference number 213 of FIG. 2A) as a cross-sectional moving image at a predetermined frame rate. The generated cross-sectional moving image is stored readably inside the signal processing unit 325.

An I/F unit 328 is configured to be connected in a communicating manner with the X-ray image processing apparatus 111 and receives information relating to X-ray images and imaging timings transmitted from the X-ray image processing apparatus 111. The X-ray images received in the I/F unit 328 are correlated with information relating to the imaging timings and held once in an X-ray image memory 329 and thereafter, they are inputted into the signal processing unit 325. The X-ray image memory 329 is thus an example of a holding unit that holds a plurality of X-ray images obtained by X-ray imaging the transmitting and receiving unit inside the body cavity in an imaging cycle defined beforehand. The I/F unit 328 is an example of a communication unit which receives the X-ray images from the X-ray image processing apparatus carrying out the X-ray imaging and holds the X-ray images in the holding unit.

In the signal processing unit 325 used in the embodiment disclosed by way of example, when the cross-sectional moving image generated based on the cross-sectional images is outputted to the LCD monitor 327, a corresponding X-ray moving image is generated and outputted. Also, when storing the cross-sectional moving image generated based on the cross-sectional images, the X-ray images are stored by being correlated for every frame. Additional details relating to these processes in the signal processing unit 325 are discussed later.

5. Features and Aspects of Optical Coherent Tomography Apparatus

Figure 4:
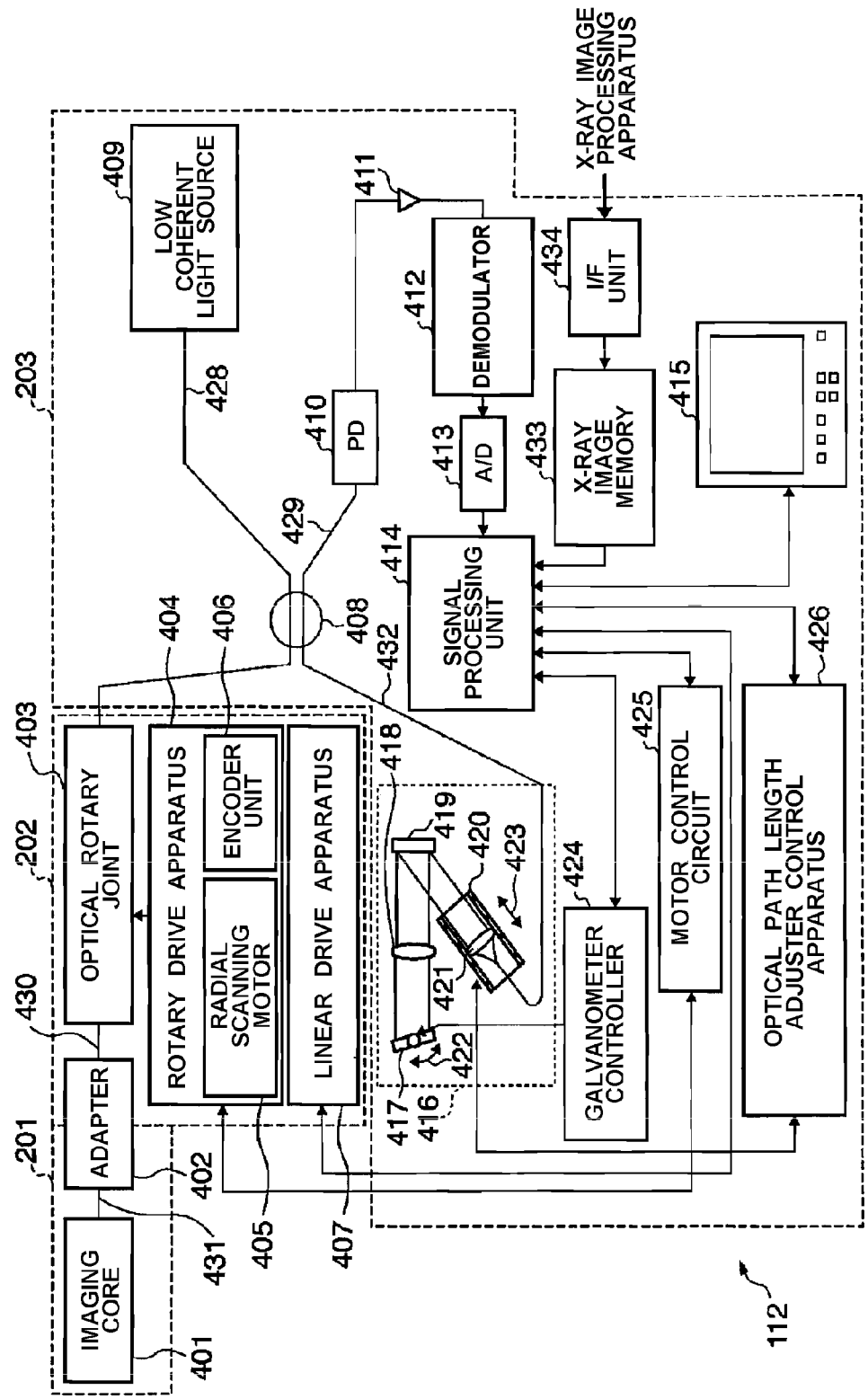
FIG. 4 is a schematic illustration of the construction of an optical coherence tomography apparatus.

Next, with respect to the imaging apparatus 112 relating to this embodiment disclosed by way of example, and referring to FIG. 4, set forth below is a description of features and aspects of the optical coherent tomography apparatus.

The apparatus includes a low coherent light source 409 of a super high luminance light-emitting diode or the like. The low coherent light source 409 outputs a low coherent light whose wavelength is around 1310 nm and which presents coherence only in such a short distance range that the coherent-able distance (coherent length) thereof is around several μm to ten and several μm.

When this light is split into two lights and thereafter are mixed, interferogram is detected when the difference of the two optical path lengths from the split point to the mixed point is within a short distance range of around several μm to ten and several μm, and when the difference of the optical path lengths is larger than that, it is never detected as interferogram.

The light of the low coherent light source 409 enters one end of a first single mode fiber 428 and is transmitted to the distal end surface side. The first single mode fiber 428 is coupled with second single mode fiber 429 and third single mode fiber 432 optically by a photo coupler unit 208 on the way.

The photo coupler unit refers to an optical component which can, for example, split one optical signal into two or more outputs, which can couple two or more inputted optical signals into one output, and so it is possible for the light of the low coherent light source 409 to be transmitted by being split into maximum three optical paths depending on aforesaid photo coupler unit 408.

The distal end side from the photo coupler unit 408 of the first single mode fiber 428 is provided with the scanner and pull-back unit 202. The inside of the scanner and pull-back unit 202 is provided with an optical rotary joint 203 which couples a non-rotation unit and a rotation unit, and which transmits light.

Further, the distal end side of a fourth single mode fiber 430 inside the optical rotary joint 403 is connected detachably with a fifth single mode fiber 431 of the optical probe unit 101 through an adaptor 402. Thus, the light from the low coherent light source 409 is transmitted to the fifth single mode fiber 431 which is inserted into the inside of the imaging core 401 including a transmitting and receiving unit which repeats transmission and reception of the light and which is drivable rotationally.

The light transmitted to the fifth single mode fiber 431 is emitted with respect to the biological tissue inside the blood vessel from the distal end side of the imaging core 401 while being scanned radially. Then, a portion of the reflected light scattered at the surface or in the inside of the biological tissue is taken-in by the imaging core 401 and returns to the first single mode fiber 428 side by way of the opposite optical path, and a portion thereof is moved to the second single mode fiber 429 side by the photo coupler unit 408, and emanated from one end of the second single mode fiber 429, whereby it is received by a photo detector, for example a photodiode 410.

The rotation unit side of the optical rotary joint 403 is driven rotationally by a radial scanning motor 405 of a rotary drive apparatus 404. Also, the rotation angle of the radial scanning motor 405 is detected by an encoder unit 406. Further, the scanner/pull-back unit 202 is provided with a linear drive apparatus 407 to effect movement (longitudinal motion) in the longitudinal direction (distal direction inside the body cavity and opposite direction thereof) of the optical probe unit 201 based on an instruction or signals from a signal processing unit 414. The longitudinal motion is realized by virtue of the linear drive apparatus 407 moving a scanner including an optical rotary joint 403 based on a control signal from the signal processing unit 414.

The distal end side (reference light path) of the photo coupler unit 408 of the second single mode fiber 429 is provided with a variable mechanism of optical path length 416 for changing the optical path length of the reference light.

This variable mechanism of optical path length 416 includes a first optical path length changing unit for high-speedily changing the optical path length corresponding to an inspection range in the depth direction (emission direction of measurement light) of the biological tissue, and a second optical path length changing unit for changing the optical path length corresponding to fluctuation of the length thereof so as to be able to absorb fluctuation in the length of individual optical probes in case of exchanging another optical probe unit for the one optical probe unit 101.

A grating 419 faces the distal end of the second single mode fiber 429, through a collimating lens 421 which is mounted on a one-axis stage 420 together with this distal end and is movable in the direction shown by an arrow 423. Also, there is mounted a minute angle rotatable galvanometer 417 as a first optical path length changing unit through this grating 419 (diffraction grating) and a corresponding lens 218. This galvanometer 417 is rotated in a high-speed manner in the direction of the arrow 422 under the control of a galvanometer controller 424.

The galvanometer 417 is a meter which reflects the light depending on a mirror of the galvanometer and is configured to rotate the mirror mounted on a movable portion thereof in a high-speed manner by applying an alternating-current drive signal to the galvanometer which functions as a reference mirror.

More specifically, a drive signal is applied to the galvanometer 417 from the galvanometer controller 424 and by rotating in a high-speed manner in the arrow 422 direction caused by the drive signal, the optical path length of the reference light changes in a high-speed manner as much as the optical path length corresponding to an inspection range in the depth direction of the biological tissue. One cycle of this change of the optical path difference becomes a period for obtaining an interferogram for one line.

On the other hand, in case of exchanging the optical probe unit 201, the one-axis stage 420 functions as a second optical path length changing unit having as much as a variable range of the optical path length, which can absorb the fluctuation of the optical path length of the optical probe unit 201. Further, the one-axis stage 420 also operates as an adjuster for adjusting an offset. For example, even in a case in which the distal end of the optical probe unit 201 is not in contact with the surface of the biological tissue, it is possible, by minutely changing the optical path length depending on the one-axis stage 420, to set a state of interfering with the reflected light from the surface position of the biological tissue.

The light whose optical path length is changed by the variable mechanism of optical path length 416 is mixed with the light obtained from the first single mode fiber 428 side by the photo coupler unit 408 provided on the way of the second single mode fiber 429 and is received by a photodiode 410 as an interferogram.

The interferogram received in the photodiode 410 in this manner is photoelectrically converted, is amplified by an amplifier 411 and thereafter, is inputted to a demodulator 412.

In the demodulator 412, a demodulation process for extracting only a signal component of the interferogram is performed and an output thereof is inputted to an A/D converter 413.

In the A/D converter 413, the interference signal is applied with sampling, for example for 200 points, and digital data of one line ("interference data") are generated. In this case, the sampling frequency becomes a value dividing one scan time period of the optical path length by 200.

The interference data of one line unit which are generated in the A/D converter 413 are inputted to a signal processing unit 414. In the signal processing unit 414, cross-sectional images at respective positions inside the blood vessel are formed based on the interference data in the depth direction of the biological tissue and thereafter, are outputted to a LCD monitor 415 as a cross-sectional moving image of a predetermined frame rate (corresponding to reference number 213 of FIG. 2A). The generated cross-sectional moving image is stored in a readable manner inside the signal processing unit 414.

An I/F unit 434 is an I/F unit configured to be connected in a communicating manner to the X-ray image processing apparatus 111 and receives information relating to X-ray images and imaging timings transmitted from the X-ray image processing apparatus 111. The X-ray images received in the I/F unit 434 are correlated with information relating to the imaging timings and held once in an X-ray image memory 433 and thereafter, they are inputted into the signal processing unit 414. The X-ray image memory 433 is a holding unit that holds a plurality of X-ray images obtained by X-ray imaging the transmitting and receiving unit inside the body cavity in an imaging cycle defined beforehand.

In the signal processing unit 414 used in the embodiment disclosed by way of example, when outputting the cross-sectional moving image generated based on the cross-sectional images to the LCD monitor 415, a corresponding X-ray moving image is generated and outputted. Also, when storing the cross-sectional moving image generated based on the cross-sectional images, the X-ray images are stored by being correlated with respective frames. Additional details of these processes in the signal processing unit 414 are discussed later.

The signal processing unit 414 is connected with an optical path length adjuster control apparatus 426, and position control of the one-axis stage 420 is carried out through the optical path length adjuster control apparatus 426. Also, the signal processing unit 414 is connected with a motor control circuit 425 and controls the rotary drive of the radial scanning motor 405.

Also, the signal processing unit 414 is connected with a galvanometer controller 424 for controlling scan of the optical path length of the reference mirror (galvanometer mirror) and receives a drive signal from the galvanometer controller 424. The motor control circuit 425 is synchronized with the galvanometer controller 424 by using the drive signal received by the signal processing unit 414.

6. Features and Aspects of Optical Frequency Domain Imaging Apparatus Utilizing Wavelength Sweep Next, within the imaging apparatuses 112 according to this embodiment representing one example of the apparatus, features and aspects of the optical frequency domain imaging apparatus utilizing wavelength sweep are discussed.

Figure 5:
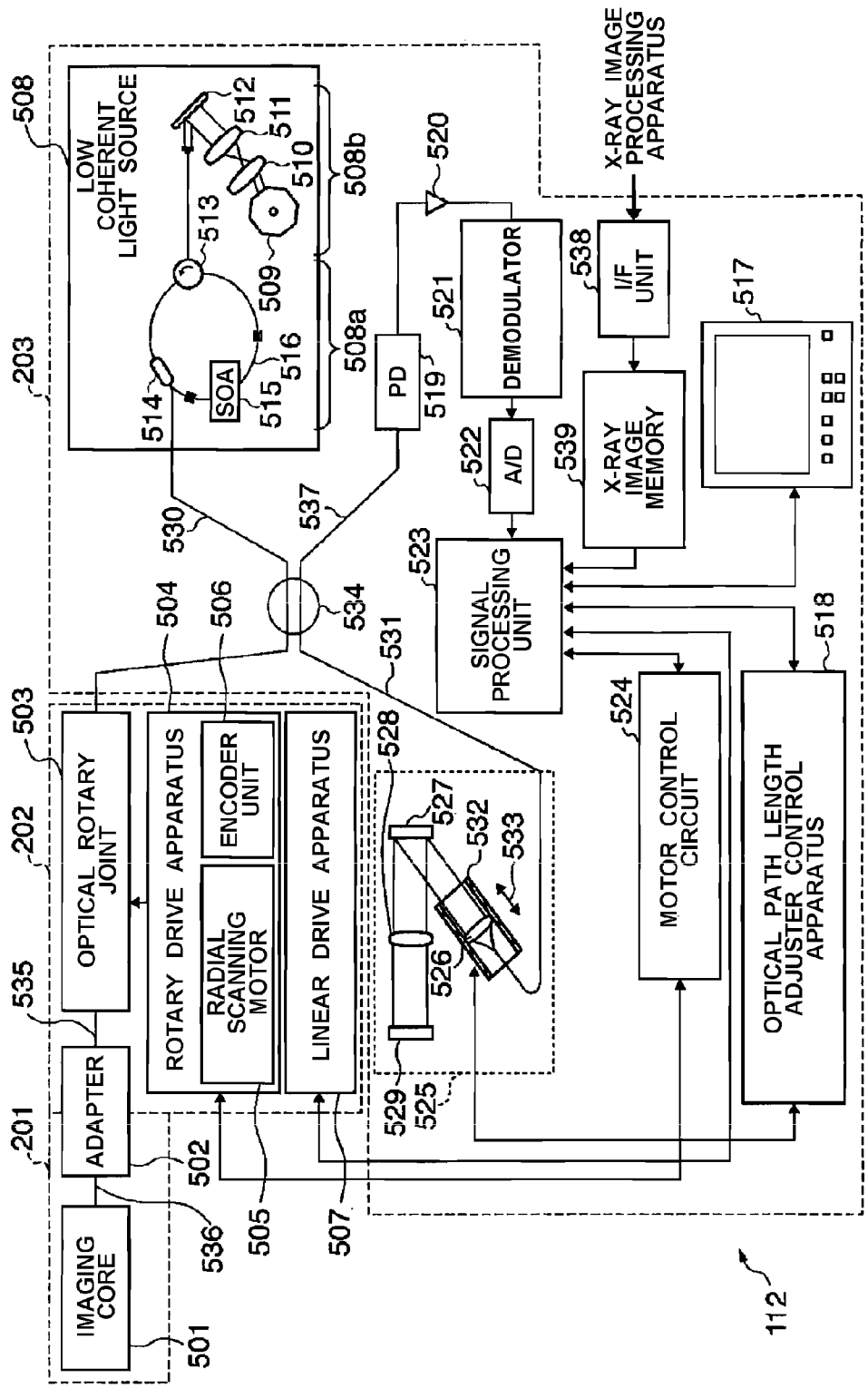
FIG. 5 is a schematic illustration of the construction of an optical frequency domain imaging apparatus utilizing wavelength sweep.

FIG. 5 schematically illustrates features and aspects of the optical frequency domain imaging apparatus utilizing wavelength sweep 112. The description which follows primarily focuses on aspects and features of the apparatus that differ from those discussed above with respect to the optical coherent tomography apparatus illustrated in FIG. 4.

The apparatus includes a wavelength swept light source 508 using a swept laser. The wavelength swept light source 508S using the swept laser is one kind of an extended-cavity laser which is composed of an optical fiber 516 coupled with a SOA 515 (semiconductor optical amplifier) in a ring shape (annular-shaped) and a polygon scanning filter (508*b*).

The light outputted from the SOA 515 advances inside the optical fiber 516 and enters into the polygon scanning filter 508*b*, the light which was wavelength-selected here is amplified by the SOA 515 and finally is outputted from a coupler 514.

In the polygon scanning filter 508*b*, the wavelength is selected by using the combination of a diffraction grating 512 for light-splitting the light and a polygon mirror 509. Specifically, the light split by the diffraction grating 512 is focused on the surface of the polygon mirror 509 by two pieces of lens (510, 511). hus, only the light having wavelength, which is perpendicular to the polygon mirror 509 returns to the same optical path and is outputted from the polygon scanning filter 508*b*, so that by rotating the mirror, it is possible to carry out time sweep of the wavelength.

With respect to the polygon mirror 509, for example, a mirror having thirty-two facets is used and a rotation speed thereof is around 50000 rpm. Depending on a unique wavelength sweep system in which the polygon mirror 509 and the diffraction grating 512 are combined, it is possible to employ wavelength sweep of a high speed and a high power output.

The light of the wavelength swept light source 508 which is outputted from the coupler 514 enters into one end of a first single mode fiber 530 and is transmitted to the distal end side. The first single mode fiber 530 is coupled optically with a second single mode fiber 537 and a third single mode fiber 531 in a photo coupler unit 534 on the way. Therefore, it is possible for the light of the wavelength swept light source 508 to be transmitted by being split into a maximum of three optical paths depending on this photo coupler unit 534.

An optical rotary joint 503 is provided on the distal end side from the photo coupler unit 534 of the first single mode fiber 530. the optical rotary joint 503 couples between a non-rotation unit and a rotation unit and which transmits the light.

Further, the distal end side of a fourth single mode fiber 535 inside the optical rotary joint 503 is detachably connected with a fifth single mode fiber 536 of the optical probe unit 201 through an optical adaptor unit 502. Thus, the light from the wavelength swept light source 508 is transmitted to the fifth single mode fiber 536 which is inserted into the imaging core 501 including a transmitting and receiving unit for repeatedly transmitting and receiving the light and which is drivable rotationally.

The transmitted light is illuminated while being radially scanned from the distal end side of the imaging core 501 with respect to the biological tissue inside the body cavity. Then, a portion of the reflected light scattered at the surface or in the inside of the biological tissue is taken-in by the imaging core 501 and returns to the first single mode fiber 530 side by way of the opposite optical path. Further, a portion thereof is moved to the second single mode fiber 537 side by the photo coupler unit 534, emanates from one end of the second single mode fiber 537, and is received by a photo detector (for example, photodiode 519).

The rotation unit side of the optical rotary joint 503 is driven rotationally by a radial scanning motor 505 of a rotary drive apparatus 504. Also, the rotation angle of the radial scanning motor 505 is detected by an encoder unit 506. Further, the scanner and pull-back unit 202 includes a linear drive apparatus 507 and defines longitudinal movement of the optical probe unit 201 based on an instruction from a signal processing unit 523.

In the imaging system 100 of this embodiment disclosed as an example, the high voltage generation apparatus 114 transmits a pulse signal for X-ray generation in synchronization with a video signal (cross-sectional moving image) to the X-ray tube 101 depending on an instruction from the X-ray image processing apparatus 111 and the X-ray is emitted to a subject body P during a certain time period. Thus, it becomes possible for a user to guide the distal end of the optical probe unit 201 to the diseased portion of blood vessel while monitoring the X-ray image of the tissue containing the blood vessel, which is displayed on the X-ray image display monitor 113.

When the distal end of the optical probe unit 201 reaches the diseased portion, the distal end of the optical probe unit 201 is further advanced slightly from (beyond) the diseased portion and stands by. Thus, it happens that the imaging core 230 lying on the distal end side of the optical probe unit 201 is positioned at an initial normal portion. At that time, on the X-ray image display monitor 113, there is also imaged an image of the imaging core in addition to an tissue image of a subject body P.

The X-ray irradiation from the X-ray tube 101 to the subject body P described above is not carried out constantly and is carried out only in a case in which it becomes necessary for the user to confirm the position of the imaging core 230 in order to minimize the dosage to which the patient is exposed.

In a state in which the imaging core 230 is positioned at the initial normal portion, the optical coherent tomography apparatus utilizing wavelength sweep starts obtaining the cross-sectional image inside the blood vessel, and the coherent light used in such a imaging apparatus has the wavelength of around 800 nm to 1550 nm and is not transmissive with respect to the blood. For this reason, on an occasion of visualizing cross-sectional images of the blood vessel, it is necessary to remove the blood inside the blood vessel beforehand from a region of a visualization target. Consequently, a physiological saline, a lactate Ringer's solution, a contrast agent and the like are discharged from the catheter and there is carried out a flush for removing the blood inside the blood vessel at the measurement region. After the flushing, the user obtains cross-sectional images of the diseased portion by carrying out a pull-back for pulling out the optical probe unit 201 at an appropriate velocity.

Also, it is possible to employ a construction in which this flushing becomes a trigger, whereby a pulse signal is transmitted to the X-ray tube 101 in order to generate the X-ray in synchronization with the video signal by an instruction from the high voltage generation apparatus 114, and the X-ray is irradiated to the subject body P. In this regard, the x-ray image processing apparatus 111 is an example of an irradiation start instruction unit which instructs irradiation start of the X-ray on an occasion of the X-ray imaging, wherein the irradiation start instruction unit instructs irradiation start of the X-ray when a flush is carried out inside the body cavity.

It is also possible to employ a construction in which the flushing, the pull-back or the X-ray irradiation of the subject body P becomes a trigger causing a command of image recording to be instructed from an image memory recording controller housed inside the X-ray image processing apparatus 111 to an image memory for X-ray, and an X-ray image is thus recorded. Such an image memory recording controller housed inside the X-ray image processing apparatus 111 is an example of a recording start instruction unit instructing start of recording of the X-ray image on an occasion of the X-ray imaging such that the trigger for the recording start instruction unit to instruct the start of the recording of the X-ray image is the flush carried out inside the body cavity.

It is further possible to employ a construction in which stopping of the pull-back becomes a trigger for stopping either the X-ray irradiation or the X-ray image, or for stopping both of them. The X-ray image processing apparatus 111 is thus an example of an irradiation stop instruction unit which instructs irradiation stop of the X-ray on an occasion of the X-ray imaging such that the X-ray image processing apparatus 111 is triggered to instruct the irradiation stop of the X-ray based on the movement stop toward the longitudinal direction (stopping of the pull-back) of the transmitting and receiving unit.

A variable mechanism of optical path length 525 is provided on the distal end side from the photo coupler unit 534 of the second single mode fiber 537. The variable mechanism of optical path length 525 permits fine-adjustment of the optical path length of the reference light.

This variable mechanism of optical path length 525 is provided with an optical path length changing unit for changing the optical path length corresponding to the length of fluctuation thereof so as to be able to absorb fluctuation of the length of the individual optical probe unit in case of using the optical probe unit 201 by being exchanged.

The third single mode fiber and a collimating lens 526 are provided on a movable one-axis stage 532 as shown by an arrow 533 in the optical axis direction thereof, and they form the optical path length changing unit.

The one-axis stage 532 operates or functions as the optical path length changing unit having a variable range of the optical path length so as to absorb fluctuation of the optical path length of the optical probe unit 201 in case of exchanging the optical probe unit 201. The one-axis stage 532 also operates as an adjuster for adjusting an offset. For example, also in a case in which the distal end of the optical probe unit 201 is not in contact with the surface of the biological tissue, it is possible, by minutely-changing the optical path length depending on the one-axis stage, to set a state of interfering with the reflected light from the surface position of the biological tissue.

The light whose optical path length is fine-adjusted by the variable mechanism of optical path length 525 is mixed with the light obtained from the first single mode fiber 530 side by the photo coupler unit 534 provided along the third single mode fiber 531 and is received by the photodiode 519 as an interferogram.

The interferogram received by the photodiode 519 in this manner is converted photoelectrically, is amplified by an amplifier 520 and thereafter, is inputted to a demodulator 521. In this demodulator 521, a demodulation process for extracting only a signal component of the interferogram is performed and an output thereof is inputted to an A/D converter 522 as an interference signal.

In the A/D converter 522, the interference signal is applied with sampling, for example, by 90 MHz for 2048 points and digital data (interference data) of one line are generated. It should be noted that the reason why the sampling frequency is set to be 90 MHz is on an assumption that about 90% of the period of wavelength sweep (25.0 µsec) is to be extracted as digital data of 2048 points in case of setting the repetition frequency of wavelength sweep to be 40 kHz and it is not limited by this aspect in particular.

The interference data of one line unit, which are generated in the A/D converter 522 are inputted to the signal processing unit 523. In the signal processing unit 523, the interference data are frequency-resolved by FFT (Fast Fourier Transform) and data in the depth direction are generated, and by coordinate-converting these data, cross-sectional images at respective positions inside the blood vessel are formed and thereafter, outputted to an LCD monitor 517 (corresponding to reference numeral 213 of FIG. 2A) as a cross-sectional moving image at a predetermined frame rate. The generated cross-sectional moving image is stored in a readable manner inside the signal processing unit 414.

The signal processing unit 523 is connected further with an optical path length adjuster control apparatus 518. The signal processing unit 523 carries out the position control of the one-axis stage 532 through the optical path length adjuster control apparatus 518.

An I/F unit 538 is an I/F unit that is configured to be connected in a communicating manner with the X-ray image processing apparatus 111 and receives information relating to X-ray images and imaging timings which are transmitted from the X-ray image processing apparatus 111. The X-ray images received in the I/F unit 538 are correlated with the information relating to the imaging timings and held once in an X-ray image memory 539 and thereafter, they are outputted to the signal processing unit 523. The X-ray image memory 539 is a holding unit that holds a plurality of X-ray images obtained by X-ray imaging the transmitting and receiving unit inside the body cavity in an imaging cycle defined beforehand.

In the signal processing unit 523 of this embodiment described as a example, when outputting the cross-sectional moving image generated based on the cross-sectional images to the LCD monitor 517, a corresponding X-ray moving image is generated and outputted. Also, when storing the cross-sectional moving image generated based on the cross-sectional images, the X-ray images are stored by being correlated with respective frames. Details of these processes in the signal processing unit 523 are discussed later.

7. Construction of Signal Processing Unit

The following description describes, in the signal processing units 325, 414, 523 of the imaging apparatus 112, the features and aspects for realizing an output process for outputting the cross-sectional moving image and the X-ray moving image to the LCD monitors 327, 415, 517, and a storage process for storing the cross-sectional moving image and the corresponding X-ray image inside the signal processing units 325, 414, 523.

Figure 6:
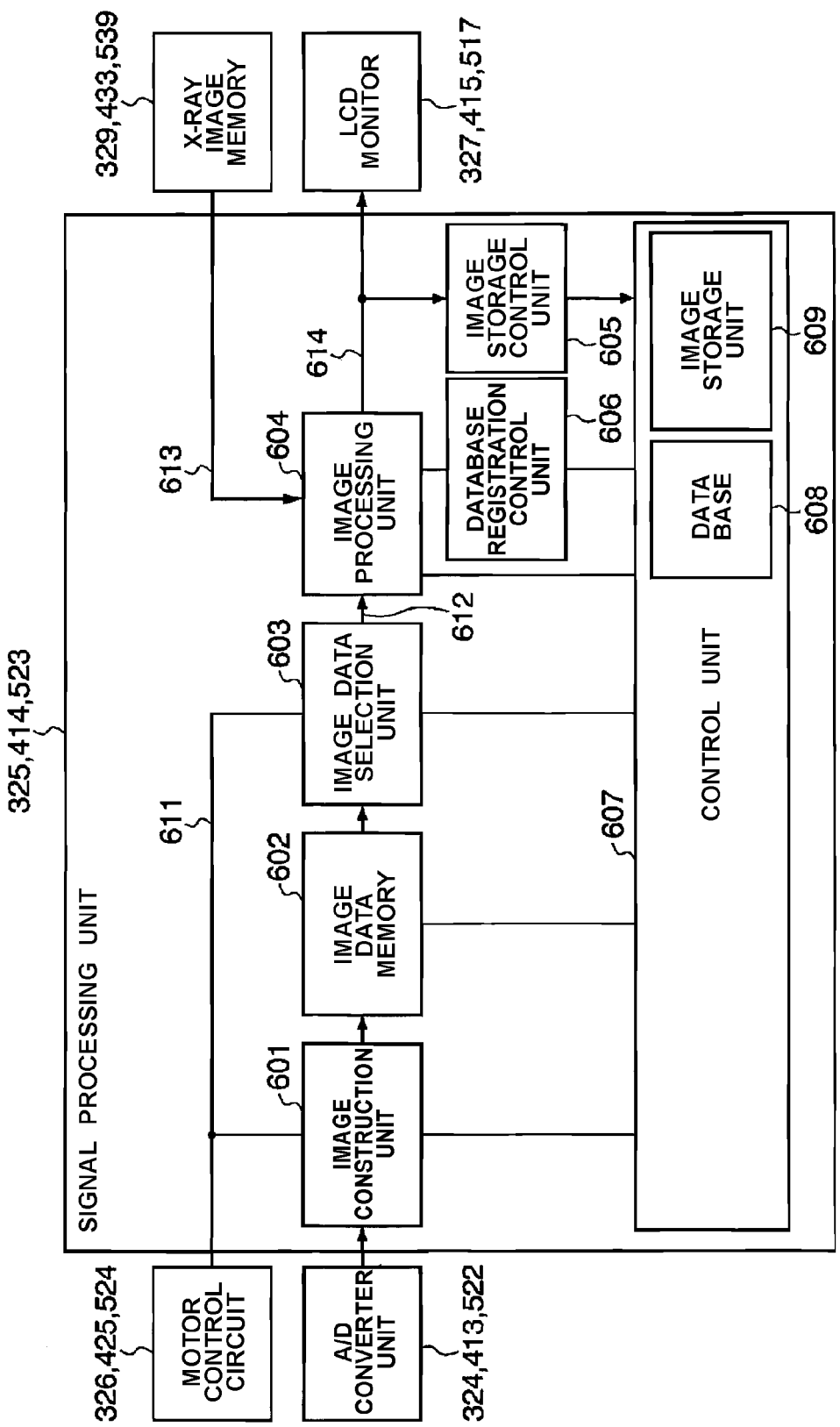
FIG. 6 is a diagram showing a detailed construction of a signal processing unit and a related function block.

FIG. 6 schematically illustrates various aspects of the signal processing units 325, 414, 523 to produce an output process and a storage process in the signal processing units 325, 414, 523 of the imaging apparatus 112. Hereinafter, for purposes of simplicity, the following discussion focuses on the signal processing unit 414 of the optical coherent tomography apparatus 112. A similar description applies to the signal processing units of the other imaging apparatus and so the following description is understood to apply to such units.

The interference data generated in the A/D converter 413 is processed in an image construction unit 601 such that the number of lines per one rotation of the radial scanning motor becomes 512 lines by using the signal of the encoder unit 406 of the radial scanning motor 405, which is outputted from the motor control circuit 425. Further, after being subjected to various kinds of processings (line addition-averaging process, filtering process and the like), the data are outputted as a cross-sectional image by polar to rectangular conversion.

The description above describes a construction in which the cross-sectional image is generated from 512 lines, but this is only an example and the apparatus is not limited in this regard.

The cross-sectional images outputted from the image construction unit 601 are held once in an image data memory 602. The image data memory 602 plays a role as a buffer in a case in which the process speed after an image data selection unit 603 is low compared with the speed by which the cross-sectional image is outputted from the image construction unit 601.

The image data selection unit 603 selects a cross-sectional image 612 to be processed in an image processing unit 604 within the cross-sectional images held once in the image data memory 602 and transmits it to the image processing unit 604.

The image processing unit 604 converts the transmitted cross-sectional image 612 to a video signal (cross-sectional moving image) at a frame rate corresponding to a signal 611 which represents rotation cycle of the encoder unit 406 and which is outputted from the motor control circuit 425.

Also, in the image processing unit 604, by reading out an X-ray image 613 from the X-ray image memory 433 based on the frame rate of the video signal (cross-sectional moving image) generated based on the cross-sectional images, the X-ray images are correlated with the respective frames of the cross-sectional moving image and a video signal (X-ray moving image) is generated based on the correlated X-ray images (here, details of correlating process for generating X-ray moving image will be mentioned later).

The image processing unit 604 serves as a first generation unit for generating a cross-sectional moving image by using the cross-sectional image generated every rotation cycle of the transmitting and receiving unit by setting the rotation cycle of the transmitting and receiving unit as the frame rate. The image processing unit 604 also operates as a second generation unit for reading out an X-ray image obtained by an X-ray imaging just previously from the X-ray image memory 329, 433, 539 at every timing for every rotation cycle of the transmitting and receiving unit and for generating an X-ray moving image by setting the rotation cycle of the transmitting and receiving unit as frame rate by using the read out X-ray image.

In the LCD monitor 415, the video signal (cross-sectional moving image) based on the cross-sectional images generated in the image processing unit 604 and the video signal (X-ray moving image) 614 based on the X-ray images are displayed in parallel.

In a database registration control unit 606, the X-ray image numbers (identification numbers) for identifying the respective X-ray images which are correlated with the respective frames of the cross-sectional moving image outputted from the image processing unit 604 are correlated with the frame numbers of the respective frames of the cross-sectional moving image and are registered in a database 608. The database 608 is an example of a registration unit which registers identification numbers for identifying X-ray images of, respective frames constituting the X-ray moving image through correlation with frame numbers of respective frames constituting the cross-sectional moving image.

In an image storage control unit 605, the cross-sectional moving images outputted from the image processing unit 604 and the respective X-ray images constituting the X-ray moving image are stored in an image storage unit 609 inside a control unit 607. Also, the cross-sectional moving image and the X-ray image, which are stored in the image storage unit 609, are read out based on the database 608, and are displayed on the LCD monitor 415 as a cross-sectional moving image and an X-ray moving image 614 respectively. The image storage unit 609 (or a part of such storage unit) serves as a first storage unit which stores the cross-sectional moving image. The image storage unit 609 (or a part of such storage unit) also serves as a second storage unit which stores the X-ray images used for the generation of the X-ray moving image.

8. Details of Correlating Process in Image Processing Unit 604

Figure 7:
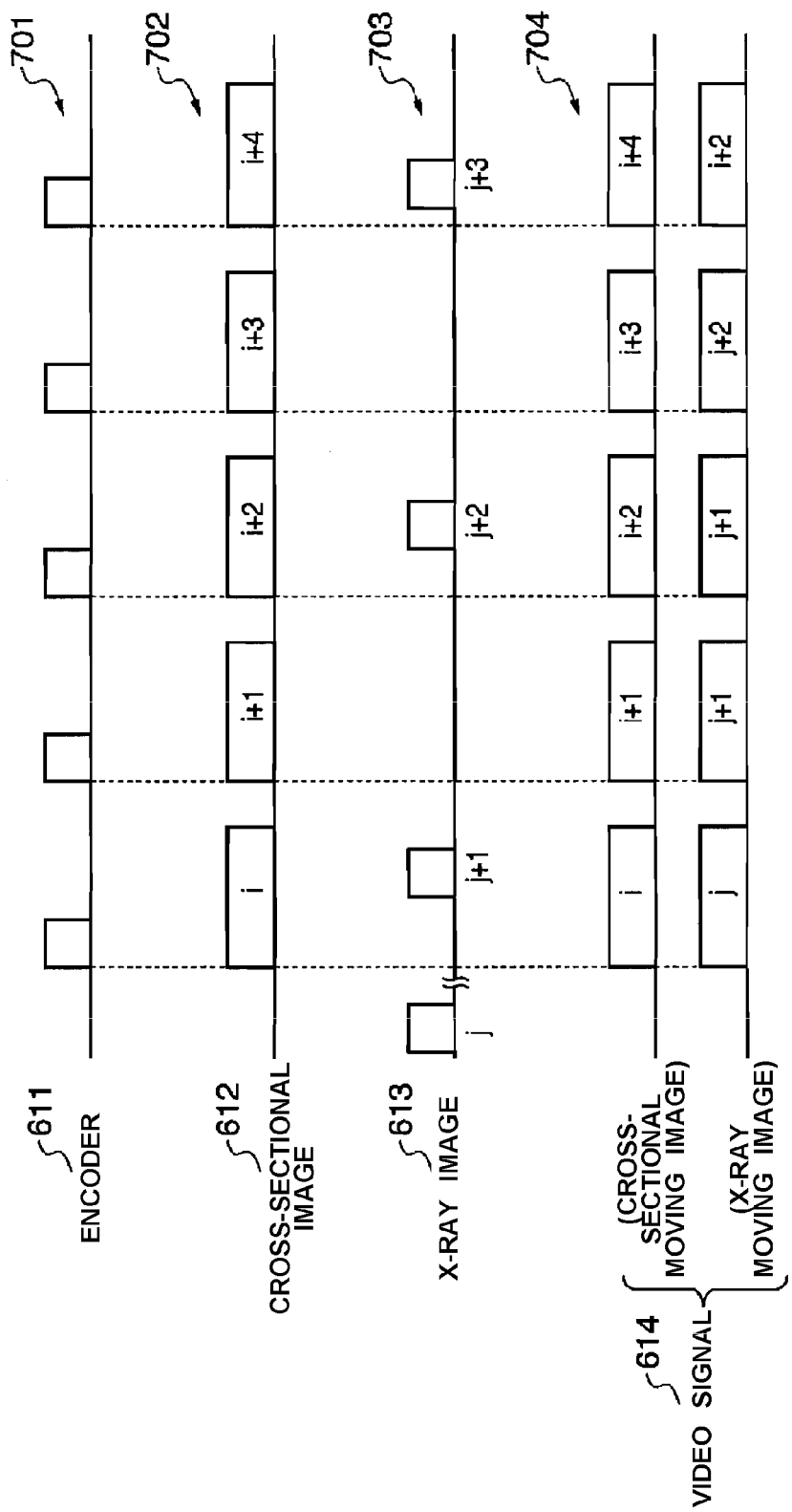
FIG. 7 is one example of a timing chart showing timing when a cross-sectional image is visualized and timing when an X-ray image is visualized.
Figure 8:
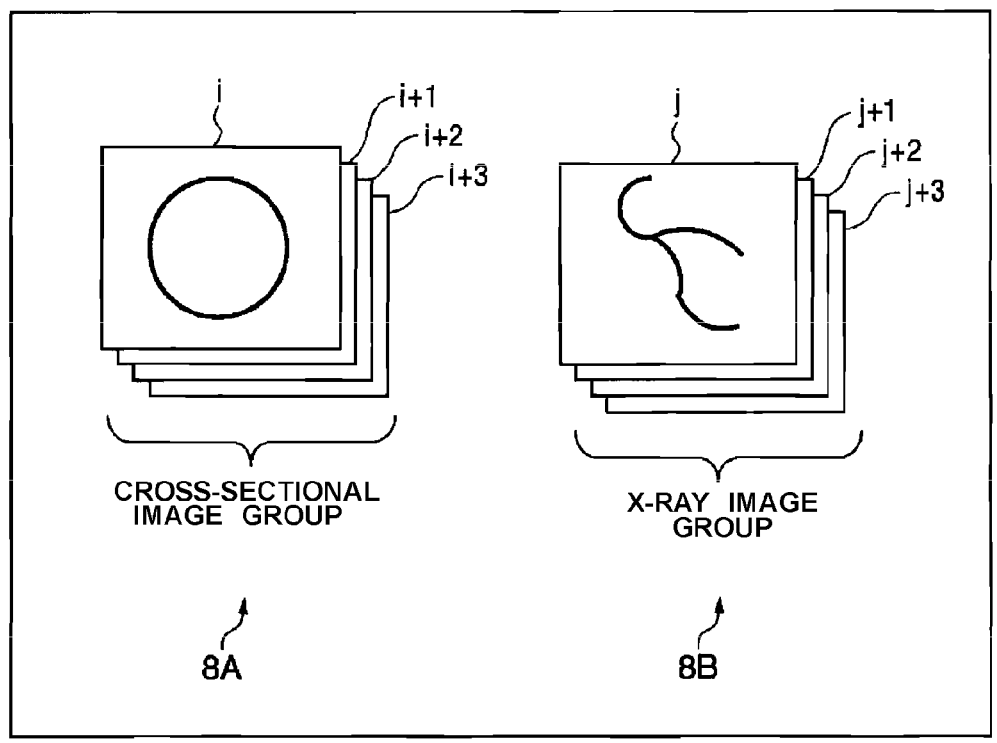
FIG. 8 is a diagram showing one example of a visualized cross-sectional image and an imaged X-ray image.

Set forth next with reference to FIG. 7 is a explanation of the correlating process carried out in the image processing unit 604. FIG. 7 illustrates an example of a timing chart 701 of the signal 611 which expresses the rotation cycle of the encoder unit 406, which is outputted from the motor control circuit 425, and an example of a timing chart 703 of a plurality of cross-sectional images 612 generated based on the signal 611. One example of the generated cross-sectional images is shown in 8A of FIG. 8.

FIG. 7 also illustrates one example of the timing chart 703 of the X-ray image 613 which is transmitted from the X-ray image processing apparatus 111. One example of the transmitted X-ray images is shown in 8B of FIG. 8.

FIG. 7 further illustrates one example of a timing chart 704 of the video signal 614 including the cross-sectional moving image which is generated based on the cross-sectional image 612 and the X-ray moving image which is generated based on the X-ray image 613.

In the example of FIG. 7, the rotation cycle outputted from the motor control circuit 425 is relatively short compared with the imaging cycle of the X-ray image 613. Consequently, in case of generating the cross-sectional moving image by frame rate based on the rotation cycle, a situation may occur in which there exists no X-ray image corresponding to a predetermined frame of the cross-sectional moving image.

Then, in the image processing unit 604, in a case in which there exists no X-ray image corresponding to a predetermined frame of the cross-sectional moving image, the X-ray moving image of frame rate based on the rotation cycle is generated by interpolation using the X-ray image which was obtained by the X-ray imaging at a previous imaging timing.

As a result, in the example of FIG. 7, the corresponding relation between the respective frames of the cross-sectional moving image and the respective frames of the X-ray moving image is as follows.

| Cross-sectional Moving Image | X-ray Moving Image |
|---|---|
| i frame | j frame |
| i + 1 frame | j + 1 frame |
| i + 2 frame | j + 1 frame |
| i + 3 frame | j + 2 frame |
| i + 4 frame | j + 2 frame |

9. Flow of Correlating Process in Image Processing Unit

Figure 9:
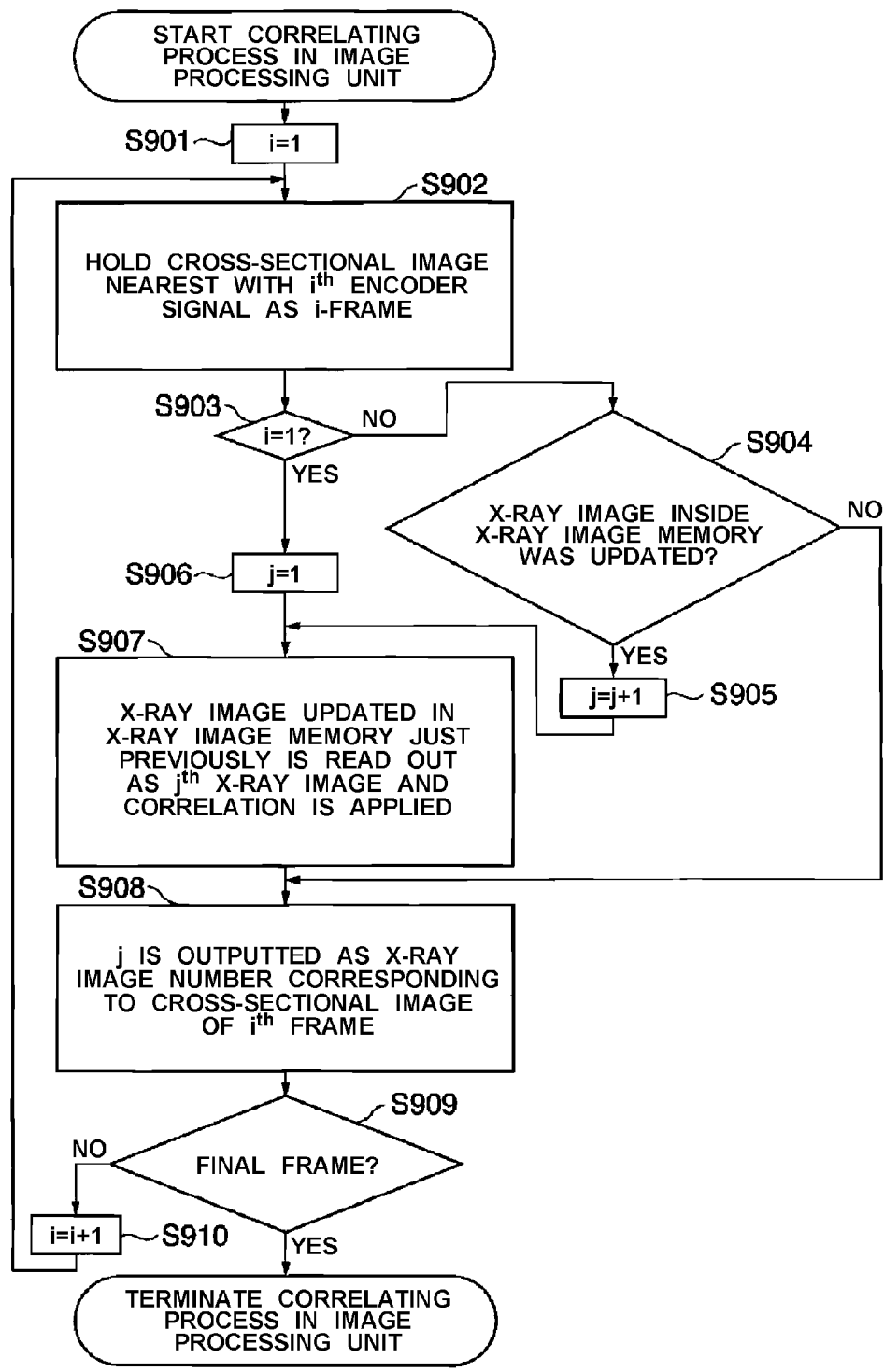
FIG. 9 is a flowchart showing a correlating process in an image processing unit.

Next, a process flow for achieving the correlating process described above in the image processing unit 604 is explained with reference to the flowchart of FIG. 9.

In step S901, "1" is assigned to parameter i for identifying the signal 611 which indicates the rotation cycle outputted from the motor control circuit 425.

In step S902, the cross-sectional image nearest the signal 611 indicating the $i^{th}$ rotation cycle is held as the i-frame.

In step S903, it is judged whether or not it is in a state in which "1" is assigned to parameter i presently. In step S903, when it is determined that i=1 is true, the flow proceeds to step S906 and "1" is assigned to parameter j for identifying the frame of the X-ray moving image and thereafter, the flow proceeds to step S907.

On the other hand, in step S903, if it is determined that i=1 is not true, the flow proceeds to step S904 and it is judged whether or not the X-ray image inside the X-ray image memory 433 is updated. When it is judged in step S904 that the X-ray image is updated, the flow proceeds to step S905 and the parameter j is incremented and thereafter the flow proceeds to step S907.

In step S907, the X-ray image which is updated just previously inside the X-ray image memory 433 is read out as $j^{th}$ X-ray image and is correlated therewith. The X-ray image which is updated just previously inside the X-ray image memory 433 is judged based on information relating to the correlated imaging timing.

In step S908, j is outputted to the database registration control unit 606 as an X-ray image number corresponding to the cross-sectional image of the $i^{th}$ frame.

In step S909, it is judged whether or not the cross-sectional moving images represent the final frame. When it is judged in step S909 that it is not the final frame, the flow proceeds to step S910 and the parameter i is incremented by one.

On the other hand, when it is judged in step S909 that it is the final frame, the correlating process is terminated.

10. Details of Database 608

The description below describes details of the database 608 generated and updated in the database registration control unit 606 by using FIG. 10.

Figure 10:
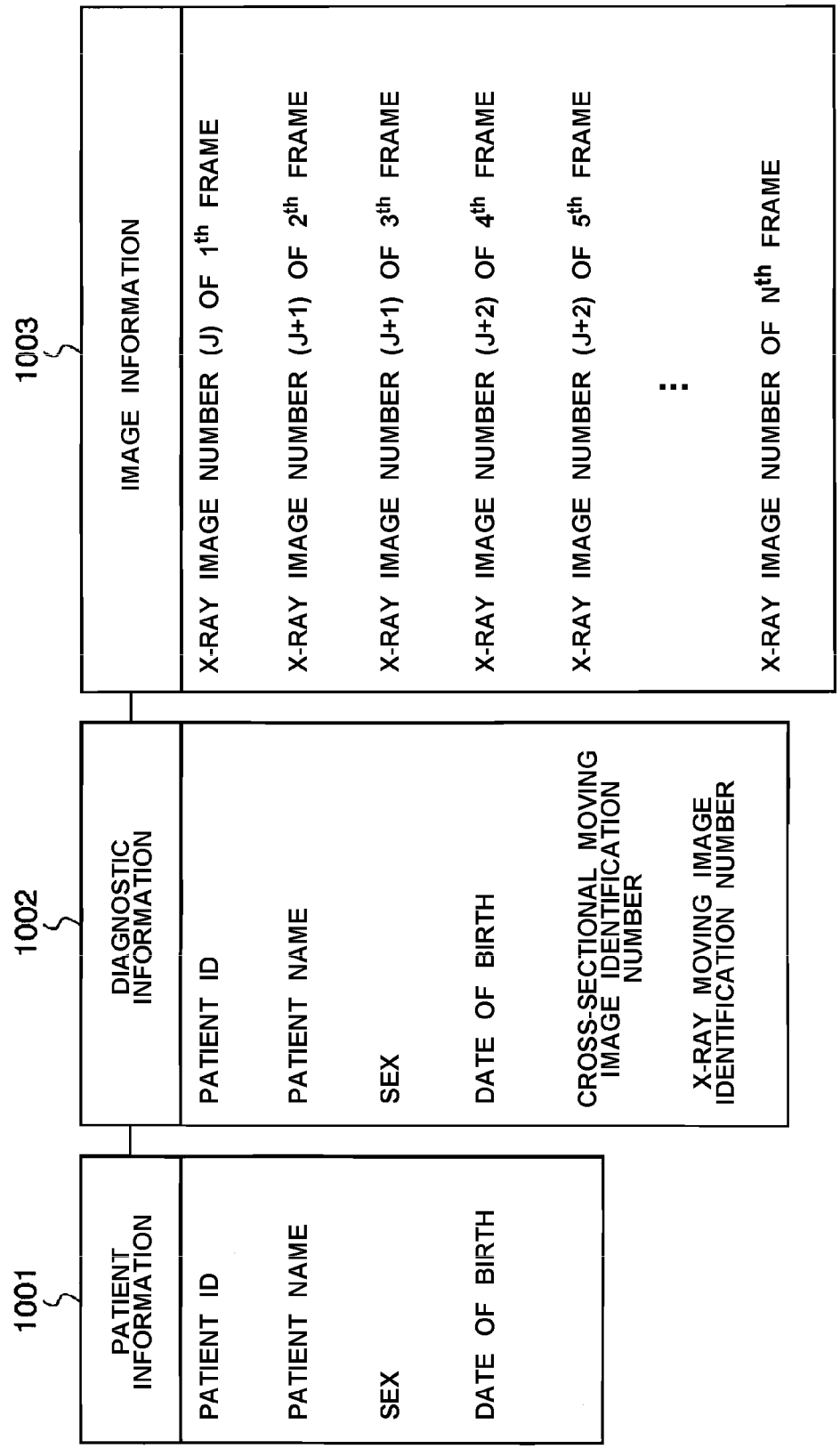
FIG. 10 is a diagram showing one example of a database.

FIG. 10 is a diagram showing one example of the database 608. As shown in FIG. 10, the database 608 is constituted by patient information 1001, diagnostic information 1002 and image information 1003.

The patient information 1001 includes information relating to a patient such as, for example, a patient ID, a patient name, sex or gender of a patient, date of birth in order to identify the patient.

The diagnostic information 1002 includes, for example, in addition to the patient ID, patient name, sex or gender of the patient and date of birth, a cross-sectional moving image identification number for specifying the cross-sectional moving image used for the diagnosis and an X-ray moving image identification number for specifying the X-ray moving image used for the diagnosis.

It is assumed that various kinds of information included in the patient information 1001 and the diagnostic information 1002 are to be registered through the control unit 607 when carrying out visualization of the cross-sectional image.

In the image information 1003, there is registered the corresponding relation in which there is indicated which frames of the cross-sectional moving image the X-ray image numbers correspond to respectively. It is assumed that the image information 1003 is to be registered by the database registration control unit 606 when the cross-sectional moving image is generated by the image processing unit 604.

By including such a construction, it is possible in the image storage control unit 605 to read out the patient information 1001 and the diagnostic information 1002 which correspond to a predetermined patient ID, and to display that information on the LCD monitor 415. Also, it is possible to read out the cross-sectional moving image of the cross-sectional moving image identification number corresponding to the aforesaid patient ID from the image storage unit 609 and to display it on the LCD monitor 415.

At that time, by reading out the X-ray image of the corresponding X-ray image number, which is registered as the image information 1003 of the database 608, from the image storage unit 609 and by displaying it on the LCD monitor 415 as each X-ray moving image, it is possible to display the X-ray moving image in synchronization with the cross-sectional moving image.

11. Display Example

Figure 11:
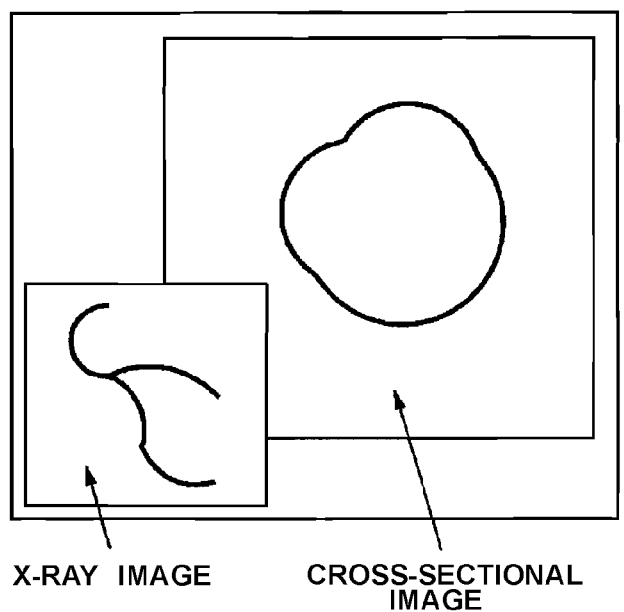
FIG. 11 is a diagram showing a display example displayed on a LCD monitor of an imaging apparatus.

FIG. 11 is a diagram showing one example of a cross-sectional moving image and an X-ray moving image which are displayed on the LCD monitor 415.

As shown in FIG. 11, by virtue of the fact that the cross-sectional moving image and the X-ray moving image, which are in synchronization with each other, are displayed on the LCD monitor 415 side by side, it becomes possible to rather easily specify which position's cross-sectional image of the blood vessel the cross-sectional image is. Also, it is possible to search a cross-sectional image at a desired position easily.

As a result thereof, according to this exemplified embodiment, it is possible to improve the usability of a user in the imaging apparatus.

Second Embodiment

In the first embodiment described above by way of example, the apparatus is configured so that the X-ray moving image is generated to conform with the frame rate of the cross-sectional moving image generated based on the rotation cycle, but the present invention is not limited in this regard, and it is possible to employ a construction in which the cross-sectional moving image is generated to conform with the frame rate of the X-ray moving image generated based on the imaging cycle of the X-ray image.

In that case, by using the cross-sectional image generated at just a previous timing at a timing for every imaging cycle of the X-ray image, this embodiment can be realized by generating the cross-sectional moving image in which the imaging cycle thereof is made to be the frame rate.

The detailed description above describes features and aspects of embodiments of an imaging apparatus and a control method disclosed by way of example. The invention is not limited, however, to the precise embodiments and variations described. Changes, modifications and equivalents can be employed by one skilled in the art without departing from the spirit and scope of the invention as defined in the appended claims. It is expressly intended that all such changes, modifications and equivalents which fall within the scope of the claims are embraced by the claims.

What is claimed is:

1. An imaging apparatus in which by moving a transmitting and receiving unit, which carries out signal transmission and reception continuously, in a longitudinal direction inside a body cavity while also rotating the transmitting and receiving unit, a reflection signal is obtained from the inside of the body cavity, and based on the obtained reflection signal, cross-sectional images of the inside of the body cavity are generated in the longitudinal direction, the imaging apparatus comprising:
   a holding unit for holding a plurality of X-ray images obtained by X-ray imaging of the transmitting and receiving unit inside the body cavity in an imaging cycle defined beforehand;
   a first generation unit for generating a cross-sectional moving image by using the cross-sectional image generated for every rotation cycle of the transmitting and receiving unit by setting the rotation cycle of the transmitting and receiving unit as a frame rate;
   a second generation unit for reading out an X-ray image obtained by an X-ray imaging just previously from the holding unit at every timing for every rotation cycle of the transmitting and receiving unit and for generating an X-ray moving image by setting the rotation cycle of the transmitting and receiving unit as the frame rate by using the read out X-ray image; and
   a display for displaying the cross-sectional moving image and the X-ray moving image at the frame rate.

2. The imaging apparatus according to claim 1, further comprising:
   a first storage unit storing the cross-sectional moving image;
   a registration unit registering identification numbers for identifying X-ray images of respective frames constituting the X-ray moving image by being correlated with frame numbers of respective frames constituting the cross-sectional moving image; and
   a second storage unit storing the X-ray images used for the generation of the X-ray moving image.

3. The imaging apparatus according to claim 2, wherein the display unit reads out the cross-sectional moving image from the first storage unit, displays it at the frame rate and concurrently, reads out the X-ray images having identification numbers registered by being correlated with frame numbers of respective frames constituting the cross-sectional moving image from the second storage unit, and displays them as the X-ray moving image at the frame rate.

4. The imaging apparatus according to claim 1, further comprising:
   an irradiation start instruction unit instructing irradiation start of the X-ray on an occasion of the X-ray imaging, wherein the irradiation start instruction unit instructs irradiation start of the X-ray when a flush is carried out inside the body cavity.

5. The imaging apparatus according to claim 1, further comprising:
   recording start instruction unit instructing start of recording of the X-ray image on an occasion of the X-ray imaging, wherein the recording start instruction unit instructs start of recording of the X-ray image, which is triggered by a fact that flush is carried out inside the body cavity.

6. The imaging apparatus according to claim 1, further comprising:
   an irradiation start instruction unit instructing irradiation start of the X-ray on an occasion of the X-ray imaging;
   a recording start instruction unit instructing start of recording of the X-ray image on an occasion of the X-ray imaging; and
   the irradiation start instruction unit and the recording start instruction unit instruct irradiation start of X-ray or start of recording of the X-ray image, which is triggered by start of movement in the longitudinal direction of the transmitting and receiving unit.

7. The imaging apparatus according to claim 1, further comprising:
   a recording start instruction unit instructing start of recording of the X-ray image on an occasion of the X-ray imaging; and
   the recording start instruction unit instructs start of recording of the X-ray image, which is triggered by irradiation start of the X-ray.

8. The imaging apparatus according to claim 1, further comprising:
   an irradiation stop instruction unit instructing irradiation stop of the X-ray on an occasion of the X-ray imaging; and
   the irradiation stop instruction unit instructs irradiation stop of the X-ray, which is triggered by movement stop toward the longitudinal direction of the transmitting and receiving unit.

9. The imaging apparatus according to claim 1, further comprising:
   a recording stop instruction unit instructing stop of recording of the X-ray image during the X-ray imaging; and
   the recording stop instruction unit instructing stop of recording of the X-ray image, which is triggered by stop of movement in the longitudinal direction of the transmitting and receiving unit.

10. The imaging apparatus according to claim 1, further comprising: a communication unit which receives the plurality of the X-ray images from X-ray image processing apparatus carrying out the X-ray imaging and for holding the plurality of the X-ray images in the holding unit.

11. The imaging apparatus according to claim 1, further comprising a contrast marker attached in the vicinity of the transmitting and receiving unit.

12. An imaging apparatus in which by moving a transmitting and receiving unit, which carries out signal transmission and reception continuously, in a longitudinal direction inside a body cavity while also rotating the transmitting and receiving unit, a reflection signal is obtained from the inside of the body cavity, and based on the obtained reflection signal, cross-sectional images of the inside of the body cavity are generated in the longitudinal direction, the imaging apparatus comprising:
   a holding unit for holding a plurality of X-ray images obtained by X-ray imaging of the transmitting and receiving unit inside the body cavity in an imaging cycle defined beforehand;
   a first generation unit for reading out the X-ray image generated for each of the imaging cycles from the holding unit by setting the imaging cycle as a frame rate and for generating an X-ray moving image,
   a second generation unit for reading out a cross-sectional image generated just previously at every timing for each of the imaging cycles and for generating a cross-sectional moving image by setting the imaging cycle as the frame rate, and a display unit for displaying the cross-sectional moving image and the X-ray moving image by the frame rate.

13. A control method for controlling an imaging apparatus in which by moving a transmitting and receiving unit, which carries out signal transmission and reception continuously, in a longitudinal direction inside a body cavity while also rotating the transmitting and receiving unit, a reflection signal is obtained from the inside of the body cavity, and based on the obtained reflection signal, cross-sectional images of the inside of the body cavity are generated in the longitudinal direction, the method comprising:

holding a plurality of X-ray images obtained by X-ray imaging the transmitting and receiving unit located inside the body cavity in an imaging cycle defined beforehand in a holding unit, generating a cross-sectional moving image by using the cross-sectional image generated for each of the rotation cycles by setting the rotation cycle of the transmitting and receiving unit as a frame rate; and reading out one of the held X-ray images obtained previously at every timing for every rotation cycle of the transmitting and receiving unit, and generating an X-ray moving image by setting the rotation cycle of the transmitting and receiving unit as the frame rate by using the read out X-ray image; and displaying the cross-sectional moving image and the X-ray moving image at the frame rate.

14. A control method for controlling an imaging apparatus in which by moving a transmitting and receiving unit, which carries out signal transmission and reception continuously, in a longitudinal direction inside a body cavity while also rotating the transmitting and receiving unit, a reflection signal is obtained from the inside of the body cavity, and based on the obtained reflection signal, cross-sectional images of the inside of the body cavity are generated in the longitudinal direction, the method comprising:

holding a plurality of X-ray images obtained by X-ray imaging the transmitting and receiving unit located inside the body cavity in an imaging cycle defined beforehand;

reading out the X-ray image generated for each of the imaging cycles by setting the imaging cycle as a frame rate, and generating an X-ray moving image;

reading out a previously generated cross-sectional image at every timing for every one of the imaging cycles and generating a cross-sectional moving image by setting the imaging cycle as the frame rate; and displaying the cross-sectional moving image and the X-ray moving image at the frame rate.

* * * * *